US011769570B2

(12) United States Patent
Sun et al.

(10) Patent No.: US 11,769,570 B2
(45) Date of Patent: Sep. 26, 2023

(54) METHOD AND SYSTEMS FOR GENOME SEQUENCE COMPRESSION

(71) Applicant: City University of Hong Kong, Hong Kong (CN)

(72) Inventors: Zhenhao Sun, Hong Kong (CN); Meng Wang, Hong Kong (CN); Shiqi Wang, Hong Kong (CN); Tak Wu Sam Kwong, Hong Kong (CN)

(73) Assignee: City University of Hong Kong, Hong Kong (CN)

( * ) Notice: Subject to any disclaimer, the term of this patent is extended or adjusted under 35 U.S.C. 154(b) by 263 days.

(21) Appl. No.: 17/445,202

(22) Filed: Aug. 17, 2021

(65) Prior Publication Data

US 2023/0076603 A1 Mar. 9, 2023

(51) Int. Cl.
| | |
|---|---|
| *H03M 7/34* | (2006.01) |
| *G16B 50/50* | (2019.01) |
| *G16B 40/20* | (2019.01) |
| *H03M 7/30* | (2006.01) |
| *G06F 16/22* | (2019.01) |
| *G06N 7/01* | (2023.01) |

(52) U.S. Cl.
CPC ......... *G16B 50/50* (2019.02); *G06F 16/2255* (2019.01); *G06N 7/01* (2023.01); *G16B 40/20* (2019.02); *H03M 7/6011* (2013.01); *H03M 7/70* (2013.01)

(58) Field of Classification Search
CPC ..... G16B 50/50; G16B 40/20; G06F 16/2255; G06N 7/01; H03M 7/6011; H03M 7/70
See application file for complete search history.

(56) References Cited

FOREIGN PATENT DOCUMENTS

WO WO-2019076177 A1 * 4/2019 ......... G06F 16/1744

OTHER PUBLICATIONS

Wang et al.; DeepDNA: A hybrid convolutional and recurrent neural network for compressing human mitochondrial genomes, IEEE International Conference on Bioinformatics and Biomedicine (BIBM). IEEE, 2018, pp. 270-274.
Goyal et al.; DeepZip: Lossless Data Compression Using Recurrent Neural Networks, Data Compression Conference, 2019, 575.

(Continued)

*Primary Examiner* — Joseph J Lauture
(74) *Attorney, Agent, or Firm* — S&F/WEHRW

(57) ABSTRACT

Systems and methods for genome sequence compression and decompression are provided. The method for compression encoding of a genome sequence includes partitioning a genome sequence into a plurality of Group of Bases (GoBs) and processing each of the plurality of GoBs independently to encode the genome sequence into a bit stream. Processing each of the plurality of GoBs includes dividing each of the plurality of GOBs into a first part and a second part, the first part including an initial context part and the second part including a learning-based inference part. The processing each of the plurality of GoBs further includes encoding the first part in accordance with a Markov model, encoding the second part in accordance with a learning-based model, and encoding the encoded first part and the encoded second part into the bit stream with an arithmetic encoder. The learning-based model may include Long and Short-Term Memory (LSTM)-based neural networks.

20 Claims, 6 Drawing Sheets

Specification includes a Sequence Listing.

(56) References Cited

OTHER PUBLICATIONS

Cui et al.; Compressing genomic sequences by using deep learning, International Conference on Artificial Neural Networks. Springer, 2020, pp. 92-104.

Wang et al.; DMcompress: Dynamic markov models for bacterial genome compression, IEEE International Conference on Bioinformatics and Biomedicine (BIBM). IEEE, 2016, pp. 776-779.

Grumbach et al.; Compression of DNA sequences, Data Compression Conference (DCC). IEEE, 1993, pp. 340-350.

Chen et al.; A compression algorithm for DNA sequences, IEEE Engineering in Medicine and biology Magazine, vol. 20, No. 4, 2001, pp. 61-66.

Pinho et al.; MFcompress: a compression tool for FASTA and multi-FASTA data, Bioinformatics, vol. 30, No. 1, 2014, pp. 117-118.

\* cited by examiner

|     | Records of probability distribution | | | |
| --- | --- | --- | --- | --- |
| 000 | A:0.01 | C:0.97 | G:0.01 | T:0.01 |
| 001 | A:0.01 | C:0.97 | G:0.01 | T:0.01 |
| 002 | A:0.002 | C:0.005 | G:0.99 | T:0.03 |
| 003 | A:0.001 | C:0.99 | G:0.003 | T:0.006 |

Input: The alphabet $\mathcal{A} = \{A, C, G, T\}$, the $k$-order Markov transition matrix M, deep estimator DM, the genome sequence $S \leftarrow a_1, a_2, \ldots, a_n$, GoB size $m$, context length $c$.
Output: Compressed Bit-stream
$b \leftarrow n/m$
//parallel
for $i \leftarrow 1$ to $b$ do
   initialize $P_1 \ldots P_k$ with prior information.
   initialize arithmetic coding.
   for $j \leftarrow k + 1$ to $c$ do
      $state \leftarrow a_{i \cdot m+j-k}, \ldots, a_{i \cdot m+j-1}$
      $P_j = M_{state}$
      $j \leftarrow j + 1$
   for $j \leftarrow c + 1$ to $m$ do
      $ctx \leftarrow a_{i \cdot m+j-c}, \ldots, a_{i \cdot m+j-1}$
      $P_j = DM_{ctx}$
      $j \leftarrow j + 1$
   Encode the probabilities to bit streams
Bit streams concatenation

FIG. 4

SEQUENCE LISTING

<160> NUMBER OF SEQ ID NOS: 22

<210> SEQ ID NO 1
<211> LENGTH: 120
<212> TYPE: DNA
<213> ORGANISM: Artificial sequence
<220> FEATURE:
<223> OTHER INFORMATION: 110; full sequence of FIG. 2 and FIG. 5.
    Synthetic nucleotide. Prepared in lab.

<400> SEQUENCE: 1
gatcacaggt ctatcaccct attaaccact cacgggagct ctccatgcat ttggtatttt      60
cgtctggggg gtatgcacgc gatagcattg cgagacgctg gagccggagc acctatgtc     120

<210> SEQ ID NO 2
<211> LENGTH: 30
<212> TYPE: DNA
<213> ORGANISM: Artificial sequence
<220> FEATURE:
<223> OTHER INFORMATION: 115a; 120 (1st line) of FIG. 1. Synthetic
    nucleotide. Prepared in lab.

<400> SEQUENCE: 2
gatcacaggt ctatcaccct attaaccact                                      30

<210> SEQ ID NO 3
<211> LENGTH: 30
<212> TYPE: DNA
<213> ORGANISM: Artificial sequence
<220> FEATURE:
<223> OTHER INFORMATION: 115b; 120 (2nd line) of FIG. 1. Synthetic
    nucleotide. Prepared in lab.

```
<400> SEQUENCE: 3
cacgggagct ctccatgcat ttggtatttt                                    30

<210> SEQ ID NO 4
<211> LENGTH: 30
<212> TYPE: DNA
<213> ORGANISM: Artificial sequence
<220> FEATURE:
<223> OTHER INFORMATION: 115c; 120 (3rd line) of FIG. 1. Synthetic
      nucleotide. Prepared in lab.

<400> SEQUENCE: 4
cgtctggggg gtatgcacgc gatagcattg                                    30

<210> SEQ ID NO 5
<211> LENGTH: 30
<212> TYPE: DNA
<213> ORGANISM: Artificial sequence
<220> FEATURE:
<223> OTHER INFORMATION: 115d; 120 (4th line) of FIG. 1. Synthetic
      nucleotide. Prepared in lab.

<400> SEQUENCE: 5
cgagacgctg gagccggagc accctatgtc                                    30

<210> SEQ ID NO 6
<211> LENGTH: 25
<212> TYPE: DNA
<213> ORGANISM: Artificial sequence
<220> FEATURE:
<223> OTHER INFORMATION: Backward part 530 (left). Synthetic nucleotide.
      Prepared in lab.

<400> SEQUENCE: 6
gatcacaggt ctatcaccct attaa                                         25

<210> SEQ ID NO 7
<211> LENGTH: 10
<212> TYPE: DNA
<213> ORGANISM: Artificial sequence
<220> FEATURE:
<223> OTHER INFORMATION: Shared context 510 (left). Synthetic
      nucleotide. Prepared in lab.

<400> SEQUENCE: 7
ccactcacgg                                                          10

<210> SEQ ID NO 8
<211> LENGTH: 25
<212> TYPE: DNA
<213> ORGANISM: Artificial sequence
<220> FEATURE:
<223> OTHER INFORMATION: Forward part 520 (left). Synthetic nucleotide.
      Prepared in lab.

<400> SEQUENCE: 8
gagctctcca tgcatttggt atttt                                         25

<210> SEQ ID NO 9
<211> LENGTH: 25
<212> TYPE: DNA
<213> ORGANISM: Artificial sequence
<220> FEATURE:
<223> OTHER INFORMATION: Backward part 530 (right). Synthetic
      nucleotide. Prepared in lab.

<400> SEQUENCE: 9
```
cgtctggggg gtatgcacgc gatag                                    25

<210> SEQ ID NO 10
<211> LENGTH: 10
<212> TYPE: DNA
<213> ORGANISM: Artificial sequence
<220> FEATURE:
<223> OTHER INFORMATION: Shared context 510 (right). Synthetic
      nucleotide. Prepared in lab.

<400> SEQUENCE: 10
cattgcgaga                                                     10

<210> SEQ ID NO 11
<211> LENGTH: 25
<212> TYPE: DNA
<213> ORGANISM: Artificial sequence
<220> FEATURE:
<223> OTHER INFORMATION: Forward part 520 (right). Synthetic nucleotide.
      Prepared in lab.

<400> SEQUENCE: 11
cgctggagcc ggagcaccct atgtc                                    25

<210> SEQ ID NO 12
<211> LENGTH: 35
<212> TYPE: DNA
<213> ORGANISM: Artificial sequence
<220> FEATURE:
<223> OTHER INFORMATION: 120 (1st line) of FIG. 5. Synthetic nucleotide.
      Prepared in lab.

<400> SEQUENCE: 12
ggcactcacc aattatccca ctatctggac actag                         35

<210> SEQ ID NO 13
<211> LENGTH: 35
<212> TYPE: DNA
<213> ORGANISM: Artificial sequence
<220> FEATURE:
<223> OTHER INFORMATION: 120 (2nd line) of FIG. 5. Synthetic nucleotide.
      Prepared in lab.

<400> SEQUENCE: 13
ccactcacgg gagctctcca tgcatttggt atttt                         35

<210> SEQ ID NO 14
<211> LENGTH: 34
<212> TYPE: DNA
<213> ORGANISM: Artificial sequence
<220> FEATURE:
<223> OTHER INFORMATION: 120 (3rd line) of FIG. 5. Synthetic nucleotide.
      Prepared in lab.

<400> SEQUENCE: 14
agagcgttac gatagcgcac gtatgggggt ctgc                          34

<210> SEQ ID NO 15
<211> LENGTH: 35
<212> TYPE: DNA
<213> ORGANISM: Artificial sequence
<220> FEATURE:
<223> OTHER INFORMATION: 120 (4th line) of FIG. 5. Synthetic nucleotide.
      Prepared in lab.

<400> SEQUENCE: 15
cattgcgaga cgctggagcc ggagcaccct atgtc    35

<210> SEQ ID NO 16
<211> LENGTH: 10
<212> TYPE: DNA
<213> ORGANISM: Artificial sequence
<220> FEATURE:
<223> OTHER INFORMATION: 610 (1st line). Synthetic nucleotide. Prepared
      in lab.

<400> SEQUENCE: 16
gatcacaggt    10

<210> SEQ ID NO 17
<211> LENGTH: 10
<212> TYPE: DNA
<213> ORGANISM: Artificial sequence
<220> FEATURE:
<223> OTHER INFORMATION: 610 (2nd line). Synthetic nucleotide. Prepared
      in lab.

<400> SEQUENCE: 17
accctattaa    10

<210> SEQ ID NO 18
<211> LENGTH: 10
<212> TYPE: DNA
<213> ORGANISM: Artificial sequence
<220> FEATURE:
<223> OTHER INFORMATION: 610 (3rd line). Synthetic nucleotide. Prepared
      in lab.

<400> SEQUENCE: 18
ccatgcattt    10

<210> SEQ ID NO 19
<211> LENGTH: 10
<212> TYPE: DNA
<213> ORGANISM: Artificial sequence
<220> FEATURE:
<223> OTHER INFORMATION: 610 (4th line). Synthetic nucleotide. Prepared
      in lab.

<400> SEQUENCE: 19
gatagcattg    10

<210> SEQ ID NO 20
<211> LENGTH: 10
<212> TYPE: DNA
<213> ORGANISM: Artificial sequence
<220> FEATURE:
<223> OTHER INFORMATION: 610 (5th line). Synthetic nucleotide. Prepared
      in lab.

<400> SEQUENCE: 20
gatcactggt    10

<210> SEQ ID NO 21
<211> LENGTH: 10
<212> TYPE: DNA
<213> ORGANISM: Artificial sequence
<220> FEATURE:
<223> OTHER INFORMATION: 610a (1st line). Synthetic nucleotide. Prepared
      in lab.

<400> SEQUENCE: 21
gagccggagc    10

```
<210> SEQ ID NO 22
<211> LENGTH: 10
<212> TYPE: DNA
<213> ORGANISM: Artificial sequence
<220> FEATURE:
<223> OTHER INFORMATION: 610a (2nd line). Synthetic nucleotide. Prepared
      in lab.

<400> SEQUENCE: 22
acttaaacac                                                          10
```

METHOD AND SYSTEMS FOR GENOME SEQUENCE COMPRESSION

REFERENCE TO SEQUENCE LISTING

The specification further incorporates by reference the Substitute Sequence Listing submitted herewith via EFS-Web on Oct. 12, 2021. The Substitute Sequence Listing text file, identified as Sub_Seq_Listing_034689-000006, is 4 kilobytes and was created on Oct. 11, 2021. The Substitute Sequence Listing, electronically filed herewith does not contain new matter.

TECHNICAL FIELD

The present invention generally relates to data compression, and more particularly relates to compression of genome sequences.

BACKGROUND OF THE DISCLOSURE

A genome is the totality of genetic material carried by an organism. The genome consists of DNA or RNA and includes both genes in the coding regions as well as non-coding DNA, mitochondrial DNA and chloroplast DNA. A genome can be described by a genome sequence which is a complete list of the nucleotides (e.g., A, C, G, and T for DNA genomes) that make up all the chromosomes of an individual or a species.

As the number of genomes being identified grows, the ability to retain the information is being strained. Currently, the number of genomes is rising rapidly (e.g., the data stored in the Shenzhen National Gene Bank reached 60 petabytes (about $6 \times 10^{16}$ bytes)). However, the cost of data storage space to store data corresponding to identified genomes is not falling at a similar rate. If data compression and transmission efficiency can be improved, millions of dollars in cloud storage transmission price can be saved.

Thus, there is a need for methods and systems to encode and decode genome sequences that provide compact compression and transmission of genome sequences. Furthermore, other desirable features and characteristics will become apparent from the subsequent detailed description and the appended claims, taken in conjunction with the accompanying drawings and this background of the disclosure.

SUMMARY

According to at least one aspect of the present embodiments, a method for compression encoding of a genome sequence is provided. The method includes partitioning a genome sequence into a plurality of Group of Bases (GoBs) and processing each of the plurality of GoBs independently to encode the genome sequence into a bit stream. Processing each of the plurality of GoBs includes dividing each of the plurality of GOBs into a first part and a second part, the first part including an initial context part and the second part including a learning-based inference part. The processing each of the plurality of GoBs further includes encoding the first part in accordance with a Markov model, encoding the second part in accordance with a learning-based model, and encoding the encoded first part and the encoded second part into the bit stream with an arithmetic encoder. The learning-based model may include Long and Short-Term Memory (LSTM)-based neural networks.

According to another aspect of the present embodiments, a method for compression decoding of a genome sequence is provided. The method includes decoding one or more controlling parameters, partitioning the bit stream into a plurality of segments based on the one or more controlling parameters, and decoding each of the multiple segments to generate one of a plurality of Group of Bases (GoBs) of a genome sequence. The decoding each of the multiple segments includes decoding each of the multiple segments through an arithmetic decoder and decoding the arithmetically decoded multiple segment by a probability estimator including a Markov model and a learning-based model to generate one of the plurality of GoBs of the genome sequence. The learning-based model may include Long and Short-Term Memory (LSTM)-based neural networks.

According to a further aspect of the present embodiments, a system for genome sequence compression is provided. The system includes a processor and a memory. The memory stores instructions which when compiled by the processor enable the processor to partition a genome sequence into a plurality of Group of Bases (GoBs) and process each of the plurality of GoBs independently to encode the genome sequence into a bit stream. The processor independently processing each of the plurality of GoBs includes dividing each of the plurality of GOBs into a first part and a second part, the first part including an initial context part and the second part including a learning-based inference part. The processor independently processing each of the plurality of GoBs further includes encoding the first part in accordance with a Markov model, encoding the second part in accordance with a learning-based model, and encoding the encoded first part and the encoded second part into the bit stream with an arithmetic encoder.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with present embodiments.

FIG. 3 is an example of a three-order transition matrix in accordance with the present embodiments.

FIG. 4 depicts an algorithm of an encoding process in accordance with the present embodiments.

12; 120 (2$^{nd}$ line)—SEQ ID NO: 13; 120 (3$^{rd}$ line)—SEQ ID NO: 14; 120 (4$^{th}$ line)—SEQ ID NO: 15.

Figure 6:
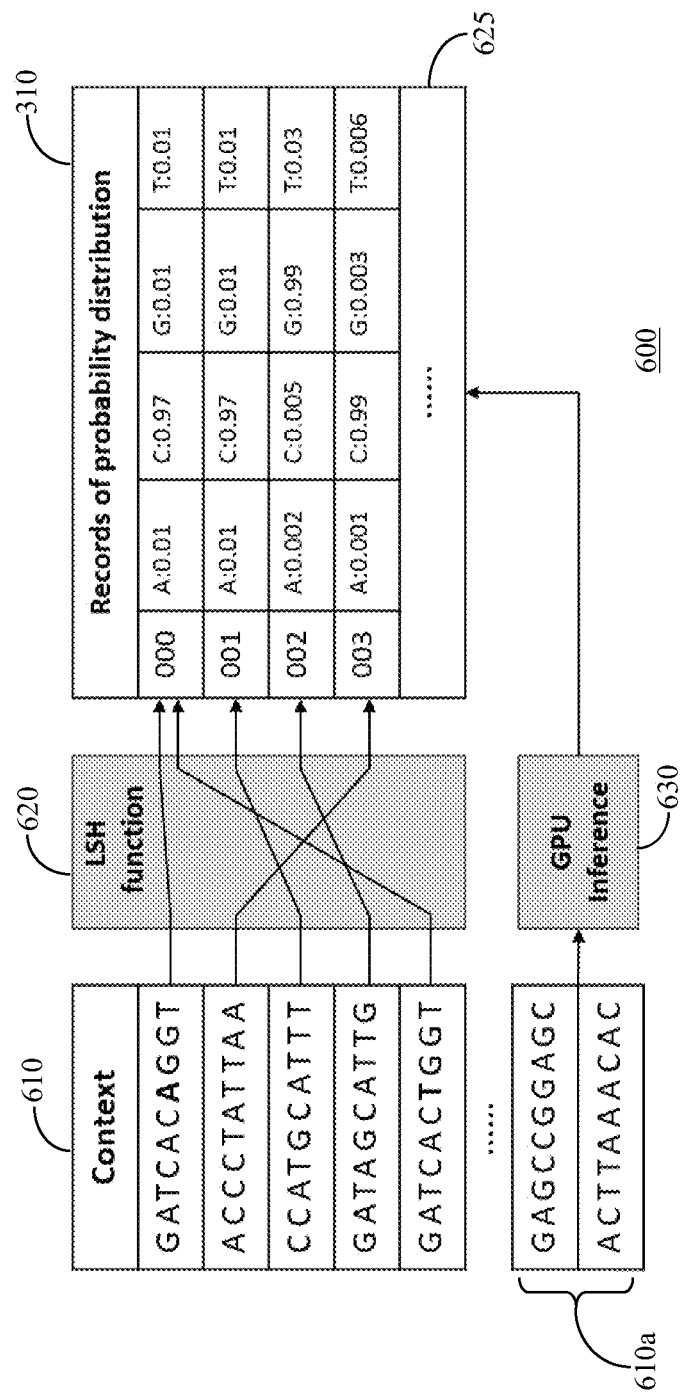

FIG. 6 depicts an illustration of encoding/decoding acceleration using locality sensitive hashing in accordance with the present embodiments. The sequences shown in the figure are as follows: 610 (1$^{st}$ line)—SEQ ID NO: 16; 610 (2$^{nd}$ line)—SEQ ID NO: 17; 610 (3$^{rd}$ line)—SEQ ID NO: 18; 610 (4$^{th}$ line)—SEQ ID NO: 19; 610 (5$^{th}$ line)—SEQ ID NO: 20; 610a (1$^{st}$ line)—SEQ ID NO: 21; 610 (2$^{nd}$ line)—SEQ ID NO: 22.

Figure 7:
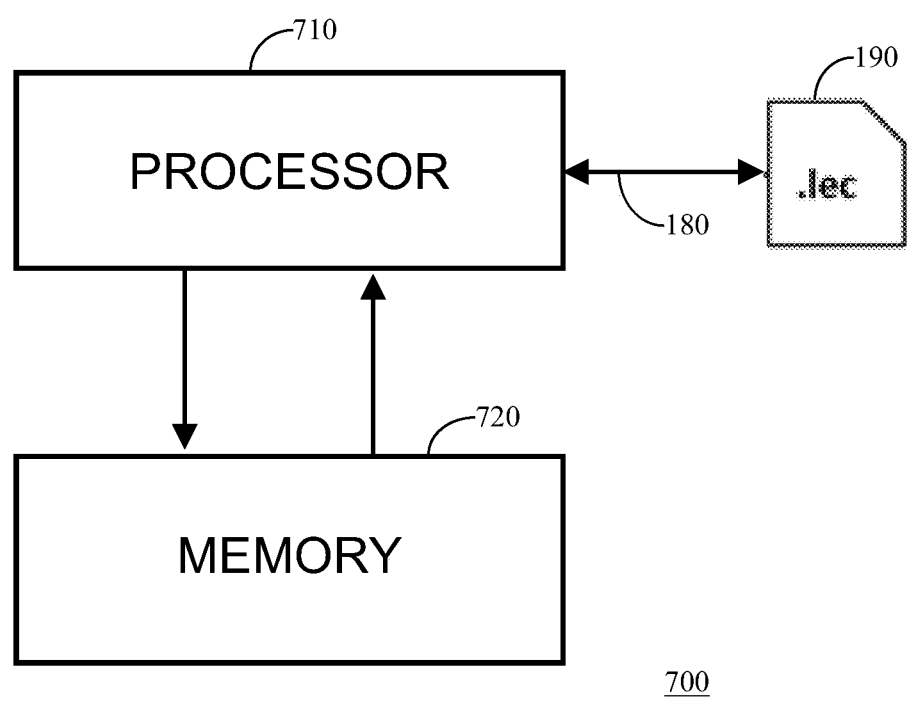

And FIG. 7 depicts a block diagram of a system for encoding and decoding genomes in accordance with the present embodiments.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of present embodiments to present a complexity configurable learning-based data compression methods and systems utilizing Markov models, Long and Short-Term Memory (LSTM)-based neural networks and arithmetic coding suitable for compressing data such as genome sequences.

In accordance with present embodiments, the concept of Group of Bases (GoB) is introduced to serve as a foundation for the systems and methods in accordance with the present embodiments and enable parallel implementation of learning-based genome sequence data compression therefor. Subsequently, a Markov model is introduced for modeling the initial content, and a learning-based inference is achieved for the remaining base data. Moreover, a bi-directional coding mode is introduced to further improve the compression ratio.

The improved compression is ultimately and advantageously achieved with efficient arithmetic coding utilizing a set of configurations on compression ratios and inference speed. As such, systems and methods in accordance with the present embodiments are shown to be more efficient and achieve flexible coding in real-world applications. To improve the encoding/decoding speed, a look-up-table is introduced to record high-frequency contexts and associated probability distributions. By combining these designs, methods and system in accordance with the present embodiments achieve a good balance between coding complexity and performance in lossless genome sequence compression.

Figure 1:
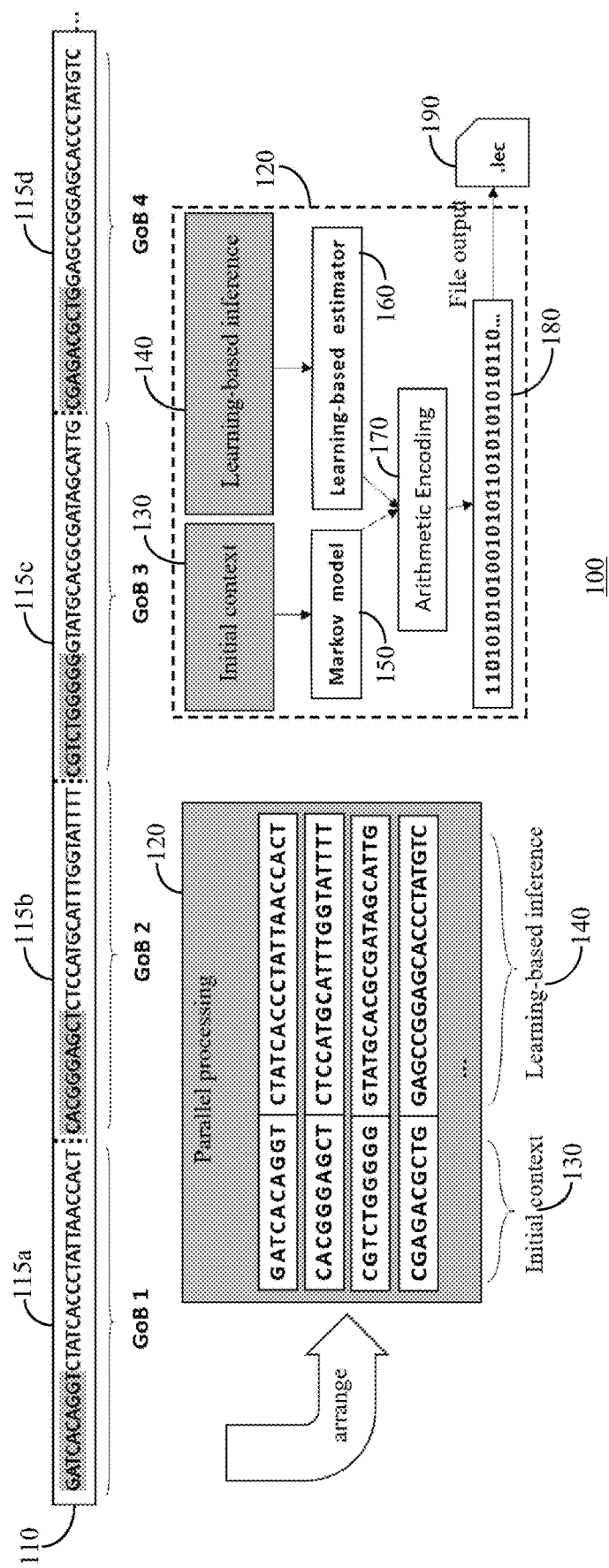
FIG. 1 is an illustration of a method for compression encoding in accordance with present embodiments. The sequences shown in the figure are as follows: 110—SEQ ID NO: 1; 115a and 120 $1^{st}$ line—SEQ ID NO: 2; 115b and 120 $2^{nd}$ line—SEQ ID NO: 3; 115c and 120 $3^{rd}$ line—SEQ ID NO: 4; 115d and 120 $4^{th}$ line—SEQ ID NO: 5.

Referring to FIG. 1, an illustration 100 depicts a method for compression encoding of a genome sequence in accordance with present embodiments. In a first step, an original genome sequence 110 (SEQ ID NO: 1) is partitioned into multiple Group of Bases (GoBs) 115a (SEQ ID NO: 2), 115b (SEQ ID NO: 3), 115c (SEQ ID NO: 4), 115d (SEQ ID NO: 5). The partitioning is user configurable and may depend on the genome species or may depend on the length of the genome sequence. The user may configure a length of all of the GoBs to be identical or not identical. If identical, each GoB may have a length $$\left\lfloor \frac{L_s}{N_g} \right\rfloor,$$

where $L_s$ is the length of the genome sequence and $N_g$ is the number of GoBs or is the number of specific base types within the genome sequence. In addition, the user may configure the GoBs to overlap one another by n bases or not overlap (i.e., where n is zero); and when overlapping, the overlap n may be any positive integer less than the number of bases in the GoBs.

The employment of GoBs in accordance with the present embodiments is treated as a coding mode and the GoB information should be signaled when encoding the genome sequence. Whether to signal an indication of the GoB may depend on the genome species, such as the indication is signaled only when the current genome sequence is one specific species or multiple specific species. Whether to signal an indication of the GoB may also depend on the length of the genome sequence. For example, the indication of the GoB may not be signaled if the length of the genome sequence is less than 64. When signaling the indication of the GoB, the GoB information in terms of the number of GoBs may be signaled or the GoB information in terms of the length of a GoB may be signaled. An indication flag for even partitioning of the GoB or for partitioning in a non-overlap manner may be signaled.

Each GoB 115a (SEQ ID NO: 2), 115b (SEQ ID NO: 3), 115c (SEQ ID NO: 4), 115d (SEQ ID NO: 5) extracted from the original genome sequence 110 (SEQ ID NO: 1) is processed independently 120 (SEQ ID Nos 2 to 5) and divided into an initial context part 130 and a learning-based inference part 140. In accordance with the present embodiments, the initial k bases of a GoB may be defined as the initial context part 130. The two parts 130, 140 are encoded with two context models of different strategies: the initial context part 130 is encoded with a low-order Markov model 150 and the learning-based inference part 140 is encoded with a learning-based model 160. The initial context part 130 may be established with a n-order Markov model for the estimation of the probability of the current base. In one example, n is a positive integer, and the n-order Markov model is built based on statistical methods. The size of the initial context part 130 is determined in accordance with an input length of the learning-based inference model 160 and this size is not user configurable. The size of the learning-based inference model 160, however, is user configurable and is determined by both the user-configurable GoB size and the size of the initial context part 130.

In a further example, the bases in a GoB may be processed sequentially where former bases are processed with the Markov model 150 and the remaining bases are processed with LSTM model 160. Alternatively, the bases in a GoB may be processed in reverse order, where the latter bases are processed with Markov model 150 and the remaining bases are processed with LSTM model 160.

With the assistant of probability distribution produced by the two context models, the bases are further encoded into a bit stream 180 with an arithmetic encoder 170. Meanwhile, controlling parameters, such as number of GoBs, context length and full length of genome, are also coded as, for example, sequence header information of the bit stream 180. The resultant bit stream 180 is then written to a file 190.

Figure 2:
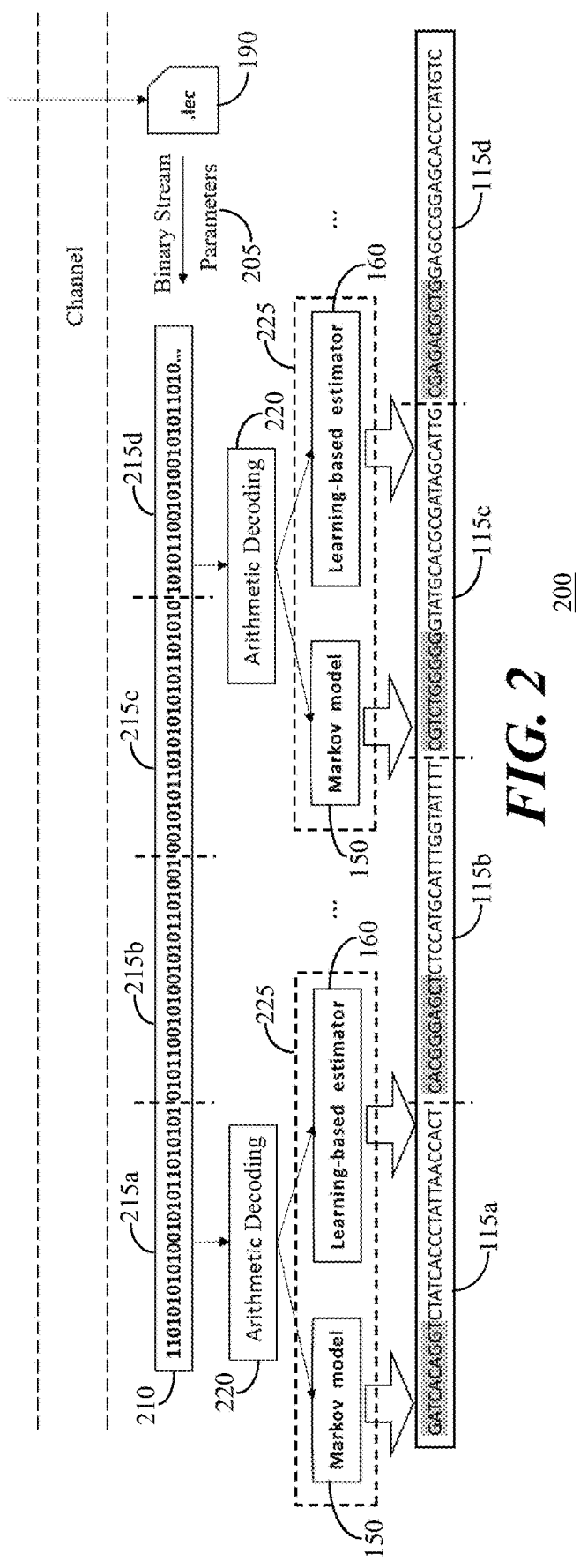
FIG. 2 is an illustration of a method for compression decoding in accordance with the present embodiments. The sequences shown in the figure are as follows: 115a—SEQ ID NO: 2; 115b—SEQ ID NO: 3; 115c—SEQ ID NO: 4; 115d—SEQ ID NO: 5; full sequence—SEQ ID NO: 1.

Referring to FIG. 2, an illustration 200 depicts a method for compression decoding of a genome sequence in accordance with present embodiments. During the compression decoding process, the controlling parameters 205 are initially parsed and decoded. Based on the controlling parameters, the bit stream 210 is partitioned into multiple segments 215a, 215b, 215c, 215d corresponding to different GoBs. As an inverse operation of the encoding process, each GoB is decoded to the original bases 115a (SEQ ID NO: 2), 115b (SEQ ID NO: 3), 115c (SEQ ID NO: 4), 115d (SEQ ID NO: 5) separately through an arithmetic decoder 220 assisted by a probability estimator 225 including the Markov model 150 and the learning-based estimator 160.

For the contextual model, previous symbols are used for predicting the probability of a current symbol, which introduces strong dependencies during the encoding and decoding phases. The encoding of a current symbol will be suspended until previous symbols are known. This strong dependency can be a barrier for parallel implementation in practice. However, motivated by the concept of Group of Pictures in video coding, the concept of Group of Bases (GoB) is applied to genome sequence compression in accordance with the present embodiments to eliminate the inter-group dependency.

More specifically, during the encoding phase in accordance with the present embodiments, the genome sequence with alphabet $\mathcal{A}=\{A,C,G,T\}$ is partitioned into multiple non-overlapping sub-sequences, where one sub-sequence is denoted as a GoB. The initial k bases of a GoB are regarded as an initial context 130 (FIG. 1). Each GoB 115a, 115b, 115c, 115d consists of m bases, which are denoted as follows, $$g_i = a_1, a_2, \ldots, a_m, a \in \mathcal{A}, i \in [1,b], \quad (1)$$

where b indicates the number of GoBs within one genome sequence. The number of GoBs may be configured by the user as an external parameter, which corresponds to the parallel number when coding one genome sequence. Each GoB includes an individual context 130, and multiple GoBs can be processed in a parallel manner (e.g., parallel processing 120) during encoding and decoding procedures, leading to the shrinkage of the overall encoding and decoding processing time. As such, parallel computing can be further boosted by involving more GoBs during the coding process. Meanwhile, users are allowed to configure the number of GoBs to obtain a desired compression ratio or coding speed. In accordance with the present embodiments, a list of configurations are preset to indicate different GoBs and to indicate the processing speed. A very-fast mode can be preset to slice the sequence data into the maximum number of GoBs, the maximum number of GoBs being generally constrained by a graphics processing unit (GPU) memory and a maximum parallel number supported by the computing devices. A very-slow mode provides the highest compression ratio with the slowest processing speed. The controlling parameters include information for decoding in accordance with the present embodiments, such as the version of the learning-based model 160, a model parameter file, the number of GoBs, the context length and the full length of genome, and are also coded into bitstream. The controlling parameters are originally stored as a json text file and are compacted together with the encoded bitstream by, for example, using a zip compressor. During the decoding phase, the controlling parameters 205 (FIG. 2) are parsed from the file header. The bitstream 210 is then partitioned into the same number of GoBs as encoded during the encoder process as determined from the decoded controlling parameters 205. Each part 215s, 215b, 215c, 215d is then decoded separately with the arithmetic decoder 220. As an inverse operation of the encoder processing, the original bases are then decoded with the exact same Markov model 150 and learning-based inference model 160.

As discussed hereinabove, the probability estimators utilized in the encoding process and the decoding process in accordance with the present embodiments include the Markov model-based estimator 150 for context initialization, and the deep model-based estimator (the learning-based model 160) used for the context modeling of the remaining symbols in a GoB.

The learning-based model 160 is expected to estimate a probability distribution of an individual symbol based on the previous c bases. However, the probability distribution of the initial c symbols is unknown. Thus, in accordance with the present embodiments, the prior probability of the first c symbols is initialized, thereby tackling the dilemma of a cold-start in a high-efficiency compression model. To initialize the probability of each symbol in the context during arithmetic coding, a low-order Markov model 150 estimates each symbol with economized computational complexity. More specifically, the Markov model 150 estimates the probability of the current base within the range of the initial k symbols, wherein the transition matrix of the Markov model 150 is obtained based on statistical methods. For an order-k Markov model, the probability of the current base $P(x_i)$ can be obtained based on prior statistical probability of previous k bases of $\{a_{i-k}, a_{i-k+1}, \ldots, a_{i-1}\}$. More specifically, the probability of a current symbol $a_i$ can be computed with conditional probability as follows, $$P(a_i | a_{i-k}, \ldots, a_{i-1}) = \frac{f_{a_{i-k+1}, \ldots, a_{i-1}, a_i}}{\sum_{x \in \mathcal{A}} f_{a_{i-k+1}, \ldots, a_{i-1}, x}}, \quad (2)$$

where $f_{a_{i-k}, \ldots, a_{i-1}, x}$ is the frequency of (k+1)—length string with $x \in \mathcal{A}$. In accordance with the concept used in the Markov model, $\{a_{i-k}, \ldots, a_{i-1}\}$ is treated as the previous state and $\{a_{i-k+1}, \ldots, a_i\}$ is treated as the current state. The transition probability corresponds to the conditional probability $P(a_i | a_{i-k}, \ldots, a_{i-1})$. Finally, a transition matrix is formed based on the transition probability through extensive statistical experiments. Referring to FIG. 3, an example of a 3-order transition matrix 300 is tabulated in a table 310, where a first column 320 represents the current state including three contextual symbols. Context and probability are included in the table 310 where the right side 330 illustrates four possible states 332, 334, 336, 338 and for any context $\{a_{i-3}, a_{i-2}, a_{i-1}\}$, the probability distribution of the current base can be determined by referring to the transition matrix 300.

The learning-based estimator 160 is designed to be an $|\mathcal{A}|$-class classification network, where $|\mathcal{A}|$ is the size of alphabet in a genome sequence. Given a context $\{a_{i-l}, a_{i-l+1}, \ldots, a_{l-1}\}$ with l bases, the learning-based estimator 160 produces a probability distribution for each symbol in alphabet $\mathcal{A}$.

Before a char-based (i.e., character-based) context $\{a_{i-l}, a_{i-l+1}, \ldots, a_{i-1}\}$ is processed by a neural network in accordance with the present embodiments, each symbol in the sequence is vectorized as a numerical vector. More specifically, each symbol in the sequence is encoded as a one-hot vector $1 \times |\mathcal{A}|$, with 1 position indicating which symbol it represents. For a c-length sequence as input, a $c \times |\mathcal{A}|$ vector can be obtained after vectorization. The one-hot vectorized context x is then processed by a convolution layer, which consists of i 1-dimension filters. This process can be described as follows, $$f_i = \sigma(W_i x + b_i), \quad (3)$$

where x is the vectorized sequence and $f_i$ is the i-th feature vector obtained from the filter $W_i$. The convolution layer is used to capture the short-term local pattern in the genome sequence. A channel-wise attention module is incorporated to measure the importance of each feature obtained from the convolution layer. After downsampling the features with a pooling layer, the features are processed by a Long and Short-Term Memory (LSTM) module. The LSTM module extends the short-term feature to a temporal long-term feature with three control gates to weight the information flow. Subsequently, two fully connected layers, which are widely used in classification tasks, are attached to the reshaped feature. Finally, the neural network outputs the probability of each symbol with a softmax layer as follows, $$y' = \sigma(x_i) = \frac{e^{x_i}}{\sum_{j=1}^{|\mathcal{A}|} e^{x_j}}, \quad (4)$$

where y' indicates the predicted probability distribution. The output values from the softmax layer are restricted between (0,1), which is in accordance with probability distribution. The network is then trained to minimize the categorical cross-entropy loss between y' and ground truth one-hot label y, $$L(y, y') = -\sum_{i}^{|\mathcal{A}|} y \cdot \log(y'). \quad (5)$$

Referring to FIG. 4, an algorithm 400 depicts an encoding process in accordance with the present embodiments. As shown in the algorithm 400, the original genome sequence S is divided into b GoBs with m bases, which are processed parallelly during the encoding and decoding phases. For the previous n−1 bases of each GoB, a statistical prior is used to initialize the probability distribution of each symbol. For the symbols from n to c, the probability distribution of current bases is obtained by referring to the transition matrix (e.g., the 3-order transition matrix 300 (FIG. 3)) of the n-order Markov model 150. For the rest of the bases of the genome, the learning-based probability estimator 160 is applied to compute the probability distribution of the current symbol. Subsequently, the arithmetic encoder 170 is incorporated to compress the sequence based on the estimated probabilities. Even though each GoB is processed individually, the bit-streams of multiple GoBs can be combined into one compressed file. The parameters such as total length of genome n, parallel number b, context length c, are indicated as the sequence header information and transmitted with the stream file.

The decoding process is exactly an inverse process of this encoding process. During the decoding phase, the header information is firstly parsed and the bit-stream in the compressed file is divided into separate streams corresponding to the GoBs based on controlling parameters decoded from the header information. Meanwhile, the Markov model 150 and the learning-based estimator 160 are triggered for context modeling. Subsequently, the arithmetic decoder is cooperated for the recovery of the base vector. With the same Markov transition matrix 300 and learning-based estimator 160, the decoder side is able to obtain the same probability estimation and recover the base index from the bit-stream. Lastly, the base index is transferred to the char format by checking the alphabet $\mathcal{A}$.

Figure 5:
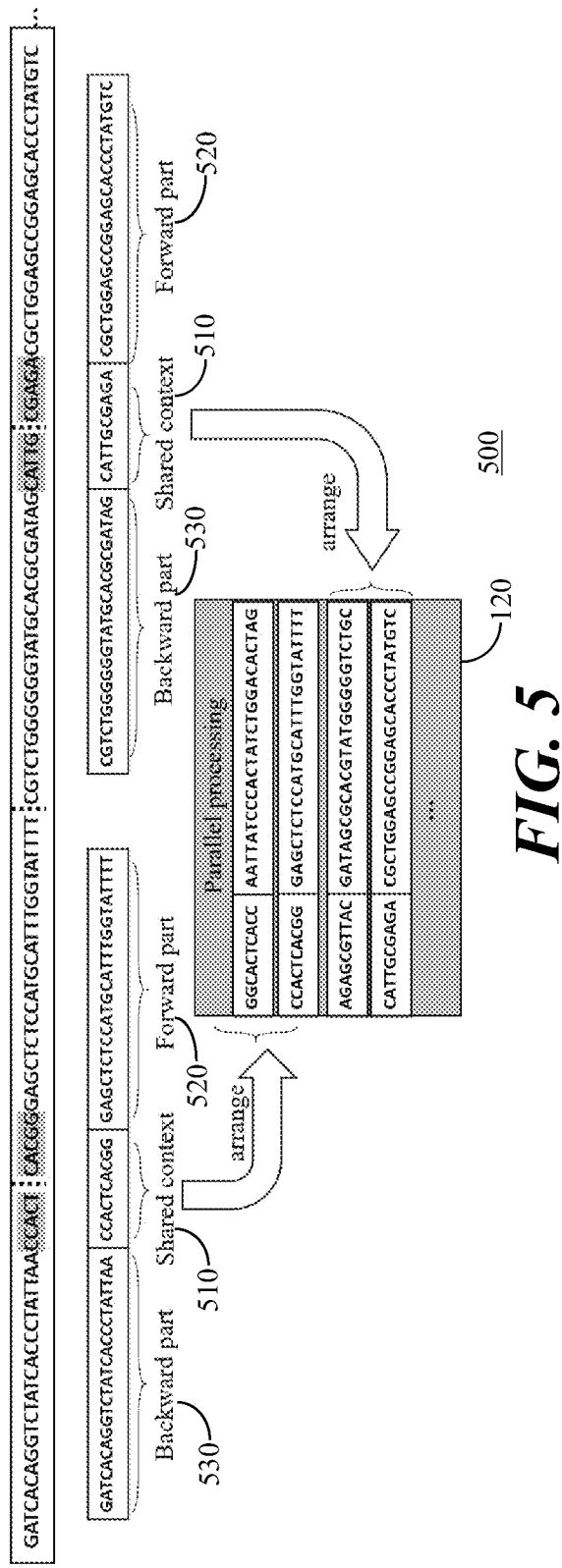
FIG. 5 is an illustration of a bi-directional coding process in accordance with the present embodiments. The sequences shown in the figure are as follows: full sequence—SEQ ID NO: 1; backward part 530 (left)—SEQ ID NO: 6; shared context 510 (left)—SEQ ID NO: 7; forward part 520 (left)—SEQ ID NO: 8; backward part 530 (right)—SEQ ID NO: 9; shared context 510 (right)—SEQ ID NO: 10; forward part 520 (right)—SEQ ID NO: 11; 120 ($1^{st}$ line)—SEQ ID NO.

In addition to the previous unidirectional coding process, a bi-directional coding process can be utilized in accordance with the present embodiments. The goal is to further reduce the contextual overhead, especially in a fast-mode compression scenario. The unidirectional coding process only predicts in a single direction, and the initial context only serves for one GoB. In the bi-directional mode, two adjacent groups share a common context, and the sharing context is the conjunction bases from two consecutive GoBs. Referring to FIG. 5, an illustration 500 depicts a bi-directional coding process in accordance with the present embodiments. A shared context 510 (SEQ ID NO: 7 or 10) regulates symbols from two GoBs as a forward part 520 (SEQ ID NO: 6 or 9) and a backward part 530 (SEQ ID NO: 8 or 11). The forward part 520 uses the same processing flow as discussed hereinabove in regards to FIG. 1. For the backward part 530, the context is reversed, and the symbol is predicted in an opposite direction. To support this mode, the learning-based model 160 will be trained with the reversed samples. Along with the existing training samples, the reversed version is supplemented to the training set as shown in FIG. 5. The bi-directional prediction mode in accordance with the present embodiments can save as much as half of the contextual overhead of encoding as compared with the encoding process 100 (FIG. 1). The length of genome sequence may be divisible by double the GoB length for the bi-directional coding process in accordance with the present embodiments. When the length of genome sequence is not divisible by double the GoB length, in accordance with the present embodiments the remainder may be larger or smaller than the GoB length.

In accordance with the present embodiments, an illustration 600 of FIG. 6 depicts encoding/decoding acceleration using locality-sensitive hashing. Since the model is based on recurrent neural networks, which require intensive calculation and become the main time-consuming process during encoding and decoding phases. The main function of the learning-based model used in accordance with the present embodiments is to infer a probability distribution based on a current context. Following the processing order, each time the context is updated, the probability calculation is carried out. A context with k bases, also referred as k-mer, may appear repetitively in the whole genome, especially when compressing multi-file genomes of a same species. Accordingly, the present embodiments introduce a look-up-table 310 to record the <context, probability distribution> item.

When building a look-up table, the size of the hash map may be problematic. The possibility of a context number grows exponentially with the number of bases in the context, thereby leading to a massive look-up table. Some of the contexts only contain several different bases because of a mutation occurring in sequence data (i.e., insert, delete, replace). As the mutations are not expected to affect the current prediction, the contexts 610 (SEQ ID Nos 16 to 20), although not exactly matching, can be successfully mapped to a same index as shown in the illustration 600. In accordance with the present embodiments, a locality-sensing hash (LSH) function 620 is designed to map the similar contexts 610 into a same location. The LSH function 620 maps similar contexts into a same probability distribution in the table 310.

In one example, the LSH table 310 is composed of fixed content (i.e., fixed contexts and probability). The LSH table 310 may have a fixed length L or a maximum length L which may be related to the length of the sequence data or related to the number of GoBs. Alternatively, the length L may be related to the initial contextual number. The LSH table 310 may be updated on-the-fly during the encoding and decoding process and, where the maximum length of the LSH table is L, the number of items exceeds L, a first-in-first-out mechanism or a first-in-last-out mechanism is used for the LSH updating. If the context is not retrieved in the LSH table 310, the LSH table 310 will be updated with new context information. And, if the context is retrieved in the LSH table 310, the associated item may be used for probability estimation in accordance with the present embodiments.

If the context (e.g., context 610a (SEQ ID Nos 21 to 22)) is not included in the table 310, the probability distribution is obtained with a GPU inference 630 and then recorded 625. The GPU inference 630 part is the same as the learning-based inference model 160, which takes a fixed-length context as input and infers a probability distribution in the GPU. When a similar context is found, the key-value pair is directly retrieved from the record. Since the look-up table 310 is maintained on-the-fly during the encoding and decoding processing, it is unnecessary to signal the table items.

Referring to FIG. 7, a system 700 for encoding and decoding genomes in accordance with the present embodiment includes a processor 710 coupled to a memory 720, the memory 720 storing compression encoding instructions in accordance with the present embodiment and the processor 710 configured to encode the genome sequence in accordance with the present embodiment. The processor 710 and the memory 720 can be part of a graphic processing unit (GPU) or may be a processor/memory combination capable of handling encoding/decoding in accordance with the present embodiments or designed specifically for such encoding/decoding. In accordance with one aspect of the present embodiments, the processor 710 can be coupled to the file 190 to provide the compressed bit stream 180 thereto or retrieve the compressed bit stream 180 therefrom.

In accordance with the present embodiments, a systematic design for genome compression, including encoder and decoder, has been provided which enables improved, robust compression of genomes. Taking advantage of the deep-learning method in accordance with the present embodiments, genomes can be encoded and decoded with relatively high predict accuracy from a given context. Furthermore, the present embodiments provide a user-configurable genome codec wherein users can customize the coding speed and the compression ratio. Also, effective coding schemes have been introduced to improve the codec speed.

The methods and systems for encoding and decoding genomes in accordance with the present embodiments support five different compression speeds (i.e., very fast, fast, medium, slow, very slow) corresponding to different compression levels, which can be configured by users, facilitating compression applications with diversified scenarios. In a test of the encoder in accordance with the present embodiments on a multi-fastA file with 1.6 million bases, the fast version of the encoding process is around 10 times faster (233.64 seconds) than the slow version (2123.34 seconds), and the compression ratios of the fast mode and the slow mode are 159.26 and 696.42, respectively.

Even in the slow mode, the methods and systems for encoding in accordance with the present embodiments is around five times faster than existing learning-based genome compression methods, such as DeepDNA. In addition, the compression ratio of the proposed model in the slow mode is 696.42, an improvement over the compression ratio of DeepDNA of 747.64. Even the fast mode encoder can achieve superior compression ratios of 159.26 as compared with the general data compressors zip and 7 zip having compression ratios of 15.39 and 153.66, respectively.

Thus, it can be seen that the methods and systems in accordance with the present embodiments propose the concept of group of bases (GoB) for parallel genome data encoding and decoding with LSTM-based neural network. By configuring the number of GoBs, five different coding complexity levels (from very-fast to very-slow) with different compression ratios (from low to high) advantageously provide more flexibility in practical applications. In addition, a Markov model for enhanced context probability estimation in accordance with the present embodiments accurately estimates the context, leading to significant improvement of compression performance, especially in the fast-encoding mode. Further, a bi-directional prediction model for learning-based inference in accordance with the present embodiments makes full use of the initial context which can additionally save about half of the contextual signaling overhead as compared with the one-direction mode for encoding and decoding in accordance with the present embodiments. A locality-sensitive hash table may also be provided during the learning-based inference in accordance with the present embodiments. The LSH function maps the similar contexts into the same probability distribution, and the retrieval time of the look-up table greatly reduces the computational cost, especially when the genomes contains repetitive contexts (e.g. when compressing multiple genome sequences from a same species).

While exemplary embodiments have been presented in the foregoing detailed description of the present embodiments, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing exemplary embodiments of the invention, it being understood that various changes may be made in the function and arrangement of steps and method of operation described in the exemplary embodiments without departing from the scope of the invention as set forth in the appended claims.

LIST OF SEQUENCES

| SEQ ID NO: | Sequence | Comment |
|---|---|---|
| 1 | GATCACAGGTCTATCACCCTATTAACCACT CACGGGAGCTCTCCATGCATTTGGTATTTT CGTCTGGGGGTATGCACGCGATAGCATTG CGAGACGCTGGAGCCGGAGCACCCTATGTC | 110; full sequence of FIG. 2 and FIG. 5 |
| 2 | GATCACAGGTCTATCACCCTATTAACCACT | 115a; 120 ($1^{st}$ line) of FIG. 1 |
| 3 | CACGGGAGCTCTCCATGCATTTGGTATTTT | 115b; 120 ($2^{nd}$ line) of FIG. 1 |
| 4 | CGTCTGGGGGTATGCACGCGATAGCATTG | 115c; 120 ($3^{rd}$ line) of FIG. 1 |
| 5 | CGAGACGCTGGAGCCGGAGCACCCTATGTC | 115d; 120 ($4^{th}$ line) of FIG. 1 |
| 6 | GATCACAGGTCTATCACCCTATTAA | Backward part 530 (left) |

LIST OF SEQUENCES

| SEQ ID NO: | Sequence | Comment |
|---|---|---|
| 7 | CCACTCACGG | Shared context 510 (left) |
| 8 | GAGCTCTCCATGCATTTGGTATTTT | Forward part 520 (left) |
| 9 | CGTCTGGGGGGTATGCACGCGATAG | Backward part 530 (right) |
| 10 | CATTGCGAGA | Shared context 510 (right) |
| 11 | CGCTGGAGCCGGAGCACCCTATGTC | Forward part 520 (right) |
| 12 | GGCACTCACCAATTATCCCACTATCTGGACACTAG | 120 (1$^{st}$ line) of FIG. 5 |
| 13 | CCACTCACGGGAGCTCTCCATGCATTTGGTATTTT | 120 (2$^{nd}$ line) of FIG. 5 |
| 14 | AGAGCGTTACGATAGCGCACGTATGGGGGTCTGC | 120 (3$^{rd}$ line) of FIG. 5 |
| 15 | CATTGCGAGACGCTGGAGCCGGAGCACCCTATGTC | 120 (4$^{th}$ line) of FIG. 5 |
| 16 | GATCACAGGT | 610 (1$^{st}$ line) |
| 17 | ACCCTATTAA | 610 (2$^{nd}$ line) |
| 18 | CCATGCATTT | 610 (3$^{rd}$ line) |
| 19 | GATAGCATTG | 610 (4$^{th}$ line) |
| 20 | GATCACTGGT | 610 (5$^{th}$ line) |
| 21 | GAGCCGGAGC | 610a (1$^{st}$ line) |
| 22 | ACTTAAACAC | 610a (2$^{nd}$ line) |

What is claimed is:

1. A method for compression encoding of a genome sequence comprising:
   partitioning a genome sequence into a plurality of Group of Bases (GoBs); and
   processing each of the plurality of GoBs independently to encode the genome sequence into a bit stream, wherein processing each of the plurality of GoBs comprises:
      dividing each of the plurality of GOBs into a first part and a second part, wherein the first part comprises an initial context part and the second part comprises a learning-based inference part;
      encoding the first part in accordance with a Markov model;
      encoding the second part in accordance with a learning-based model; and
      encoding the encoded first part and the encoded second part into the bit stream with an arithmetic encoder.

2. The method in accordance with claim 1 further comprising:
   determining controlling parameters based on the genome sequence and the plurality of GoBs; and
   encoding the controlling parameters as a part of the bit stream.

3. The method in accordance with claim 2 wherein encoding the controlling parameters comprises encoding the controlling parameters as header information of the bit stream.

4. The method in accordance with claim 2 wherein the controlling parameters include one or more of number of GoBs, context length, and full length of the genome sequence.

5. The method in accordance with claim 1 wherein the learning-based model comprises Long and Short-Term Memory (LSTM)-based neural networks.

6. The method in accordance with claim 1 wherein a number or length of the plurality of Group of Bases (GoBs) is user configurable to vary coding complexity level and/or compression ratios.

7. The method in accordance with claim 1 wherein the second part comprises a forward part connected to a first end of the initial context part and a backward part connected to a second end of the initial context part, and wherein encoding the second part comprises bi-directionally parallel processing the forward part and the backward part in accordance with the learning-based model.

8. The method in accordance with claim 1 wherein encoding the second part comprises:
   defining a locality-sensitive hash table; and
   thereafter using the locality-sensitive hash table as a look-up table for encoding the second part in accordance with the learning-based model.

9. A method for compression decoding of a bit stream comprising a compressed genome sequence comprising:
   decoding one or more controlling parameters;
   partitioning the bit stream into a plurality of segments based on the one or more controlling parameters;
   decoding each of the multiple segments to generate one of a plurality of Group of Bases (GoBs) of a genome sequence, wherein decoding each of the multiple segments comprises:
      decoding each of the multiple segments through an arithmetic decoder; and
      decoding the arithmetically decoded multiple segment by a probability estimator including a Markov model and a learning-based model to generate one of the plurality of GoBs of the genome sequence.

10. The method in accordance with claim 9 wherein decoding the one or more controlling parameters comprises decoding the one or more controlling parameters from header information of the bit stream.

11. The method in accordance with claim 9 wherein the one or more controlling parameters include one or more of number of GoBs, context length, and full length of the genome sequence.

12. The method in accordance with claim 9 wherein the learning-based model comprises Long and Short-Term Memory (LSTM)-based neural networks.

13. The method in accordance with claim 9 wherein the plurality of Group of Bases (GoBs) is user configurable to vary coding complexity level and/or compression ratios.

14. A system for genome sequence compression comprising:
   a processor; and
   a memory coupled to the processor, wherein the memory stores instructions which when compiled by the processor enable the processor to:
      partition a genome sequence into a plurality of Group of Bases (GoBs); and
      process each of the plurality of GoBs independently to encode the genome sequence into a bit stream, wherein independent processing each of the plurality of GoBs comprises:
         dividing each of the plurality of GOBs into a first part and a second part, wherein the first part comprises an initial context part and the second part comprises a learning-based inference part;
         encoding the first part in accordance with a Markov model;
         encoding the second part in accordance with a learning-based model; and
         encoding the encoded first part and the encoded second part into the bit stream with an arithmetic encoder.

15. The system in accordance with claim 14 wherein the instructions further enable the processor to:
    determine controlling parameters based on the genome sequence and the plurality of GoBs; and
    encode the controlling parameters as a part of the bit stream.

16. The system in accordance with claim 14 wherein the second part comprises a forward part connected to a first end of the initial context part and a backward part connected to a second end of the initial context part, and
    wherein encoding the second part comprises bi-directionally parallel processing the forward part and the backward part in accordance with the learning-based model.

17. The system in accordance with claim 14 wherein encoding the second part comprises:
    defining a locality-sensitive hash table; and
    thereafter using the locality-sensitive hash table as a look-up table for encoding the second part in accordance with the learning-based model.

18. The system in accordance with claim 14 wherein the instructions further enable the processor to:
    decode of a bit stream comprising a compressed genome sequence by:
        decoding one or more controlling parameters;
        partitioning the bit stream into a plurality of segments based on the one or more controlling parameters;
        decoding each of the multiple segments to generate one of a plurality of Group of Bases (GoBs) of a decoded genome sequence, wherein decoding each of the multiple segments comprises:
            decoding each of the multiple segments through an arithmetic decoder;
            decoding the arithmetically decoded multiple segment by a probability estimator including the Markov model and the learning-based model to generate one of the plurality of GoBs of the genome sequence.

19. A non-transient computer readable medium containing program instructions for causing a computer to perform the method of claim 1.

20. A non-transient computer readable medium containing program instructions for causing a computer to perform the method of claim 9.

* * * * *